United States Patent [19]

Dickoré et al.

[11] 4,057,417
[45] Nov. 8, 1977

[54] 6-SEC.-BUTYL-1,2,4-TRIAZIN-5(4H)-ONE COMPOUNDS AND HERBICIDAL COMPOSITIONS

[75] Inventors: Karlfried Dickoré, Leverkusen; Ludwig Eue; Robert Rudolf Schmidt, both of Cologne, all of Germany

[73] Assignee: Bayer Aktiengesellschaft, Leverkusen, Germany

[21] Appl. No.: 562,293

[22] Filed: Mar. 26, 1975

[30] Foreign Application Priority Data

Apr. 10, 1974 Germany .............................. 2417511

[51] Int. Cl.$^2$ .......................... A01N 9/22; A01N 9/00; C07D 253/06
[52] U.S. Cl. ........................................... 71/93; 71/88; 544/182
[58] Field of Search ................. 71/93, 88; 260/240 G, 260/248 AS

[56] References Cited

U.S. PATENT DOCUMENTS

| 3,671,523 | 6/1972 | Westphal et al. | 71/93 |
| 3,821,219 | 6/1974 | Lin | 71/93 |
| 3,847,914 | 11/1974 | Dickore et al. | 71/93 |
| 3,905,801 | 9/1975 | Fawzi | 71/93 |
| 3,961,936 | 6/1976 | Westphal et al. | 71/93 |

Primary Examiner—Glennon H. Hollrah
Attorney, Agent, or Firm—Burgess, Dinklage & Sprung

[57] ABSTRACT

New 6-sec.-butyl-1,2,4-triazin-5(4H)-one compounds of the formula:

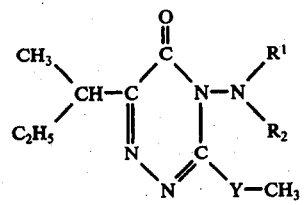

(I)

wherein
R$^1$ and R$^2$ are each hydrogen, or
R$^1$ and R$^2$ together represent alkylidene or substituted alkylidene of the formula:

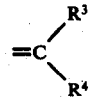

wherein R$^3$ is hydrogen, alkyl or cycloalkyl, and
R$^4$ is alkyl, alkenyl, cycloalkyl, cycloalkenyl, aralkyl, aralkenyl, optionally substituted aryl or an optionally substituted heterocyclic radical, or
R$^3$ and R$^4$ together with the carbon atom shown from a 5-membered to 7-membered ring, and
Y is sulfur, NH or NCH$_3$;
are outstandingly active herbicides.

13 Claims, No Drawings

6-SEC.-BUTYL-1,2,4-TRIAZIN-5(4H)-ONE COMPOUNDS AND HERBICIDAL COMPOSITIONS

The present invention relates to certain new 6-sec.-butyl-1,2,4-triazin-5(4H)-one compounds, and to herbicidal compositions and uses thereof.

It is known that certain 6-butyl-1,2,4-triazin-5(4H)-ones, namely 6-iso-butyl- and 6-tert.-butyl-3-methylthio-4-amino-1,2,4-triazin-5(4H)-one, can be used as selective herbicides (compare U.S. Pat. No. 3,671,523). However, the selective herbicidal activity of these preparations, especially against weeds and wild grasses which are difficult to combat, is not always satisfactory if low amounts are used. Against cleavers (Galium aparine) the above-mentioned 1,2,4-triazin-5-ones are insufficiently active even if rather large amounts are used.

The present invention provides 6-sec.-butyl-1,2,4-triazin-5(4H)-ones of the general formula:

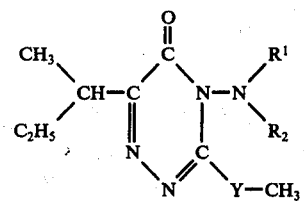

wherein
R¹ and R² are each hydrogen, or
R¹ and R² together represent alkylidene or substituted alkylidene of the formula:

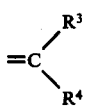

wherein
R³ is hydrogen, alkyl or cycloalkyl, and
R⁴ is alkyl, alkenyl, cycloalkyl, cycloalkenyl, aralkyl, aralkenyl, optionally substituted aryl or an optionally substituted heterocyclic radical, or
R³ and R⁴ together with the carbon atom shown form a 5-membered to 7-membered ring, and
Y is sulfur, NH or NCH₃.

Preferably, R³ is hydrogen, alkyl of up to 6 carbon atoms or cycloalkyl of 3 to 7 carbon atoms, especially hydrogen or methyl, and R⁴ is alkyl or alkenyl of up to 6 carbon atoms, cycloalkyl or cycloalkenyl of 3 to 7 carbon atoms, aralkyl, aralkenyl, aryl or substituted aryl of up to 10 carbon atoms, a heterocyclic radical or a substituted heterocyclic radical, especially alkyl with 1 to 6 carbon atoms, phenyl or furyl; or R³ and R⁴ conjointly represent —(CH₂)ₙ—, with n denoting 4 or 5.

Surprisingly, the 1,2,4-triazin-5-(4H)-ones, of the formula (I) exhibit not only a very broad action against weeds but also a particularly powerful herbicidal activity even against cleavers (Galium aparine), which are difficult to combat.

This activity was unforeseeable to those skilled in the art since the chemically nearest 1,2,4-triazin-5(4H)-ones previously know, which are substituted in the 6-position by isobutyl or tert.-butyl radicals, do not possess this property. The 6-sec.-butyl-1,2,4-triazin-5(4H)-ones according to the invention accordingly represent a valuable addition to the range of agents for combating weeds.

The invention also provides a process for the production of a compound of formula (I) wherein
a. when the compound is a 4-amino-6-sec.-butyl-3-methylthio-1,2,4-triazin-5(4H)-one of the formula (I) wherein
Y is sulfur, and
R¹ and R² are each hydrogen,
a 4-amino-6-sec.-butyl-3-thioxo-1,2,4-triazin-5(2H,4H)-one of the formula:

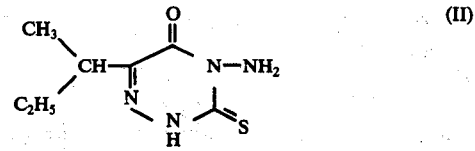

is reacted with a methylating agent of the formula:

wherein
X represents chlorine, bromine, iodine or SO₄CH₃, in the presence of an acid-binding agent;

b. when the compound is a 3,4-diamino-6-sec.-butyl-1,2,4-triazin-5-(4H)-one of the formula (I) wherein
Y is NH or NCH₃, and
R¹ and R² are each hydrogen,
1. a 4-amino-6-sec.-butyl-3-methylthio-1,2,4-triazin-5(4H)-one of the formula (I),
wherein
Y is sulfur, and
R¹ and R² are each hydrogen,
is reacted with an amine of the general formula:

wherein
R⁵ is hydrogen or methyl,
optionally in the presence of a diluent, or
2. a diaminoguanidine of the formula:

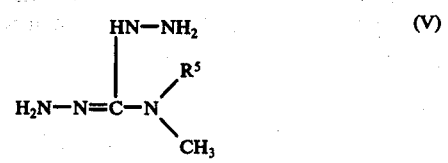

wherein
R⁵ is hydrogen or methyl,
is reacted with a carboxylic acid of the general formula:

wherein
Z is oxygen or sulfur,
optionally in the presence of a diluent;

c. when the compound is a 4-alkylideneamino-6-sec.-butyl-1,2,4-triazin-5(4H)-one of the formula (I), wherein R¹ and R² together represent alkylidene $$=C\begin{matrix}R^3\\R^4\end{matrix}$$

and

Y is sulfur, NH or NCH₃, a 4-amino-6-sec.-butyl-1,2,4-triazin-5(4H)-one of the formula (I),
wherein
R¹ and R² are each hydrogen
is reacted with an oxo compound of the general formula:

$$O=C\begin{matrix}R^3\\R^4\end{matrix} \quad (VII)$$

wherein
R³ and R⁴ have the above-mentioned meanings,
optionally in the presence of a diluent.

If 4-amino-6-sec.-butyl-3-thioxo-1,2,4-triazin-5-(2H,4H)-one and methyl iodide are used as starting materials, the course of the reaction can be represented by the following equation:

 +CH₃I ⟶

If 4-amino-6-sec.-butyl-3-methylthio-1,2,4-triazin-5(4H)-one and monomethylamine are used as starting materials, the course of the reaction can be represented by the following equation:

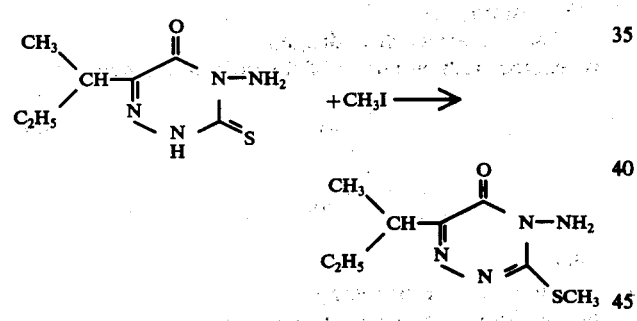

If N,N'-diamino-N''-methylguanidine and 3-methyl-2-oxo-valeric acid are used as starting materials, the course of the reaction can be represented by the following equation:

$$\begin{matrix}HN-NH_2\\|\\H_2N-N=C-NH-CH_3\end{matrix} + \begin{matrix}CH_3\\C_2H_5\end{matrix}CH-CO-COOH \longrightarrow$$

[structure of product]

If 4-amino-6-sec.-butyl-3-methylthio-1,2,4-triazin-5(4H)-one and isobutyraldehyde are used as starting materials, the course of the reaction can be represented by the following equation:

[structure] + OCH—CH(CH₃)₂ ⟶

[structure]

If 3-dimethylamino-4-amino-6-sec.-butyl-1,2,4-triazin-5(4H)-one and acetone are used as starting materials, the course of the reaction can be represented by the following equation:

[structure] + O=C(CH₃)₂ ⟶

[structure]

Methylating agents of the formula (III) include methyl chloride, methyl bromide, methyl iodide and dimethyl sulfate.

Amines of the formula (IV) include monomethylamine and dimethylamine.

Diaminoguanidines of the formula (V) include N,N'-diamino-N''-methylguanidine and N,N'-diamino-N''-dimethylguanidine.

Carboxylic acids of the formula (VI) include 3-methyl-2-oxo-valeric acid and 3-methyl-2-thioxo-valeric acid.

The following may be mentioned as examples of oxo compounds of the formula (VII) which can be used in the process of the invention: acetaldehyde, propionaldehyde, n-butyraldehyde, isobutyraldehyde, acetone, methyl ethyl ketone, diethyl ketone, cyclopentanone, cyclohexanone, cycloheptanone, hexahydrobenzaldehyde, hexahydrotolyl-4-aldehyde, tetrahydrotolyl-4-aldehyde, cinnamaldehyde, hydrocinnamaldehyde, benzaldehyde, 4-hydroxybenzaldehyde, 4-methoxybenzaldehyde, 4-chlorobenzaldehyde, 3-chlorobenzaldehyde, 2-chlorobenzaldehyde, 3-nitrobenzaldehyde, 4-nitrobenzaldehyde, salicylaldehyde, furfuraldehyde, 5-nitro-furane-2-aldehyde, thiophene-2-aldehyde, pyridine-2-aldehyde, pyridine-3-aldehyde, pyridine-4-aldehyde, methylisopropyl ketone, methyl isobutyl ketone, acetophenone, 3-nitroacetophenone, 4-chloroacetophenone and hexahydroacetophenone.

The 4-amino-6-sec.-butyl-3-thioxo-1,2,4-triazin-5(2H,4H)-one of the formula (II), used as a starting material, was not previously known. It can be prepared for example by reacting a carboxylic acid of the formula (VI) with thio-carbohydrazide, in accordance with a known type of reaction (compare Chem. Berichte 97, page 2173 (1964)). 3-Methyl-2-thioxo-valeric acid of the formula (VI), wherein Z represents sulfur, was also not previously known. It can be prepared for example in accordance with a known type of reaction by condensation of methyl ethyl ketone with rhodanine, a N-substituted rhodanine or 2,4-dioxo-1,3-thiazolidine, and alkaline hydrolysis of the condensation product (compare Helv. Chim. Acta 5, 610 (1922); Ibid. 6, 458, 467 (1923); Bull. Soc. Chim. France 1948/1120).

In carrying out the process according to the invention for the preparation of 4-amino-6-sec.-butyl-3-methyl-thio-1,2,4-triazin-5(4H)-one of the formula (I), wherein Y represents sulfur and R¹ and R² represent hydrogen, 1 − 5 mols of the methylating agent of the formula (III) are usually added to a solution of one mol of 4-amino-6-sec.-butyl-3-thioxo-1,2,4-triazin-5(2H,4H)-one in one mol of aqueous sodium hydroxide solution or potassium hydroxide solution. The reaction is generally carried out at 0° to 100° C, preferably 20° to 50° C, and at pressures of 0.5 to 5 atmospheres, preferably at normal pressure. The reaction product precipitates from the solution and may be isolated in the usual manner.

In carrying out the process according to the invention for the preparation of 3,4-diamino-6-sec.-butyl-1,2,4-triazin-5(4H)-ones of the formula (I), wherein Y represents NH or NCH₃ and R¹ and R² represent hydrogen, one mol of 4-amino-6-sec.-butyl-3-methylthio-1,2,4-triazin-5(4H)-one is usually reacted with one to 20 mols, preferably 1 to 3 mols, of an amine of the formula (IV) at 20°–150° C, preferably 60°–80° C. Solvents which can be used include alcohols such as methanol, ethanol, isopropanol or butanol. The addition of organic acids such as acetic acid, propionic acid or p-toluenesulfonic acid, in amounts of 0.1 to 10 mols, preferably of 1 to 2 mols, increases the reaction rate. The reaction is generally carried out at pressures of 1–10 atmospheres, preferably at normal pressure. The reaction products can be isolated by evaporating off the solvents used and neutralising the acids which may have been used, after stirring with water.

Furthermore, 3,4-diamino-6-sec.-butyl-1,2,4-triazin-5(4H)-ones of formula (I), wherein Y, R¹ and R² have the above-mentioned meanings, can be obtained by reaction of a diaminoguanidine of the formula (V) or of one of its salts with a carboxylic acid of the formula (VI). This process is carried out by stirring molar amounts of the components in aqueous or alcoholic solution at temperatures of 20°–100° C, preferably 40°–80° C. Salts of the diaminoguanidine of the formula (V) which can be used include salts with organic or inorganic acids such as acetic acid, p-toluenesulfonic acid, hydrochloric acid and sulfuric acid.

In carrying out the process according to the invention for the preparation of 4-alkylideneamino-6-sec.-butyl-1,2,4-triazin-5(4H)-ones of the formula (I), wherein Y represents S, NH or NHCH₃ and R¹ and R² conjointly represent alkylidene of the formula

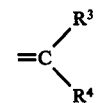

with R³ and R⁴ having the above-mentioned meaning, 1 to 20 mols, preferably 1 to 5 mols, of an oxo compound of the formula (VII) are usually employed per mol of a compound of the formula (I), in which R¹ and R² represent hydrogen. The reaction can be carried out in all inert organic solvents, such as hydrocarbons, chlorinated hydrocarbons, ethers or alcohols, in the temperature range of 0°–150° C, preferably in the range 20°–80° C. It is also possible to employ an excess of the oxo compound to be used, without additional solvent. The reaction rate is increased by adding catalytic amounts of inorganic or organic acids such as hydrochloric acid, sulfuric acid, phosphoric acid, toluene-sulfonic acid, methanesulfonic acid, acetic acid, trifluoroacetic acid or acid ion exchangers. These acids are generally used in a molar ratio of 1:0.001 to 1:0.1. For working up, the reaction products may be isolated by low temperature crystallization or by evaporation of the solvent or of the excess oxo compound.

The following examples are given for the purpose of illustrating the preparation of the compounds used in the present invention:

EXAMPLE 1

Preparation of 4-amino-6-sec.-butyl-3-methylthio-1,2,4-triazin-5(4H)-one

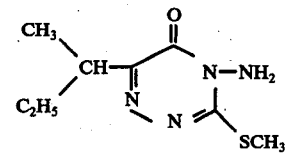

66 ml of methyl iodide were added to a solution of 200 g of 4-amino-6-sec.-butyl-3-thioxo-1,2,4-triazin-5(2H,4H)-one in a solution of 40 g of sodium hydroxide in 1 liter of water, at 20° C, whilst stirring. When the slightly exothermic reaction had subsided, stirring was continued until the pH value reached 7 − 8 and the reaction product which had crystallized out was filtered off and washed with cold water. After drying, 205 g (96%) of 4-amino-6-sec.-butyl-3-methylthio-1,2,4-triazin-5(4H)-one were obtained, melting point 60° C (from carbon tetrachloride/petroleum ether).

4-Amino-6-n-butyl-3-methylthio-1,2,4-triazin-5(4H)-one, melting point 79° C (from methylcyclohexane), which was used as the comparison agent, was obtained analogously by starting from 4-amino-6-n-butyl-3-thioxo-1,2,4-triazin-5(2H,4H)-one.

4-Amino-6-sec.-butyl-3-thioxo-1,2,4-triazin-5(2H,4H)-one used as the starting material, was obtained as follows: 106 g of thiocarbohydrazide were added to a solution of 130 g of 3-methyl-2-oxo-valeric acid in 1 liter of 1.2 normal sodium hydroxide solution, and 80 ml of acetic acid were added dropwise at 60°–80° C. The reaction product which crystallized out was filtered off, washed repeatedly with water and dried in vacuo at 60° C. 195 g (98%) of melting point 111° C (from toluene) were obtained.

4-Amino-6-n-butyl-3-thioxo-1,2,4-triazin-5(2H,4H)-one was obtained analogously by starting from 2-oxo-caproic acid or the equivalent amount of 2-thioxo-caproic acid. Melting point 131° C (from methanol).

EXAMPLE 2

Preparation of 4-benzylideneamino-6-sec.-butyl-3-methylthio-1,2,4-triazin-5(4H)-one

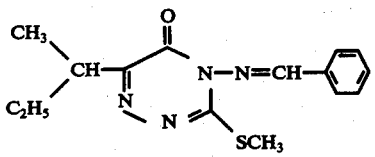

21.4 g of 4-amino-6-sec.-butyl-3-methylthio-1,2,4-triazin-5(4H)-one and 11.0 ml of benzaldehyde, dissolved in 50 ml of isopropanol, were briefly heated to the reflux temperature after adding 0.1 g of p-toluenesulfonic acid. On cooling to 0° C, 23.2 g of crude product crystallized out and were purified further by dissolving in 200 ml of boiling toluene. A small amount of a high-melting by-product crystallized out at 0° C and was filtered off and discarded. On concentration on a rotary evaporator, the mother liquor left 21.1 g (70%) of a pale oil which crystallized after trituration with a little methanol. The pure 4-benzylideneamino-6-sec.-butyl-3-methylthio-1,2,4-triazine-5 (4H)-one melted at 73° C.

EXAMPLE 3

Preparation of 4-isobutylideneamino-6-sec.-butyl-3-methylthio-1,2,4-triazin-5(4H)-one

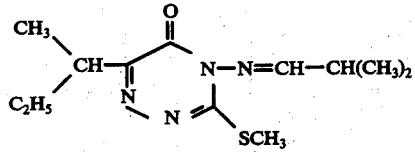

42.8 g of 4-amino-6-sec.-butyl-3-methylthio-1,2,4-triazin-5(4H)-one were dissolved in 60 ml of isobutyraldehyde. 0.2 g of p-toluenesulfonic acid was added, the mixture was stirred until the slightly exothermic reaction had subsided and was diluted with 200 ml of methylene chloride, and the whole was stirred with 100 ml of water, containing 0.5 g of sodium carbonate. The organic phase was separated off, washed with water and concentrated on a rotary evaporator. The residue which remained consisted of 52.0 g (97.5%) of 4-isobutylideneamino-6-sec.-butyl-3-methylthio-1,2,4-triazin-5(4H)-one, melting point 16° C (from pentane); $n_D^{20}$ 1.5493.

EXAMPLE 4

Preparation of 4-furfurylidene-amino-6-sec.-butyl-3-methylthio-1,2,4-triazin-5(4H)-one

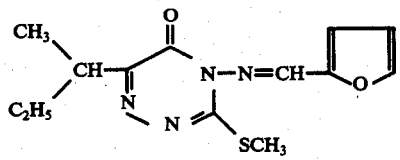

17.5 ml of freshly distilled furfuraldehyde and 3.8 g of p-toluenesulfonic acid were added to a solution of 42.8 g of 4-amino-6-sec.-butyl-3-methylthio-1,2,4-triazin-5(4H)-one in 200 ml of methanol. The mixture was left to stand overnight at room temperature and was then stirred with 1 liter of 1% strength sodium carbonate solution, the product was taken up in 100 ml of methylene chloride and the organic phase was separated off. After evaporation of the solvent, 58.1 g (100%) of an oil which gradually solidified were obtained. After recrystallization from a little methanol or from cyclohexane, 39 g (67%) of pure 4-furfurylidene-amino-5-sec.-butyl-3-methylthio-1,2,4-triazin-5(4H)-one of melting point 92° C can be isolated.

EXAMPLE 5

Preparation of 4-amino-6-sec.-butyl-3-methylamino-1,2,4-triazin-5(4H)-one

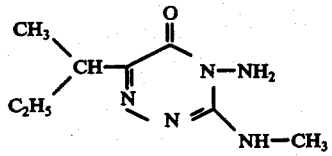

Monomethylamine was passed for 4 hours into a boiling solution of 42.8 g of 4-amino-6-sec.-butyl-3-methylthio-1,2,4-triazin-5(4H)-one of which 12 ml of glacial acetic acid and 1 g of p-toluenesulfonic acid had been added, and the mixture was then boiled for a further 4 hours under reflux. The solvent was largely evaporated off in vacuo and the oily residue was taken up in methylene chloride and repeatedly shaken with 10% strength sodium carbonate solution. The organic phase was separated off and concentrated by evaporation. 38.6 g (98% of theory) of 4-amino-6-sec.-butyl-3-methylamino-1,2,4-triazin-5(4H)-one which gradually solidified, remained. The product was purified further by recrystallization from carbon tetrachloride. Melting point = 117° C.

EXAMPLE 6

Preparation of 4-amino-6-sec.-butyl-3-dimethylamino-1,2,4-triazin-5(4H)-one

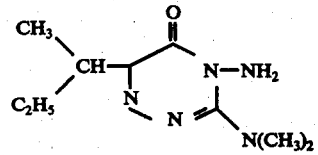

Analogously to the procedure described in Example 5, reaction of 42.8 g of 4-amino-6-sec.-butyl-3-methylthio-1,2,4-triazin-5(4H)-one with dimethylamine gave 39.4 g (93% of theory) of 4-amino-6-sec.-butyl-3-dimethylamino-1,2,4-triazin-5(4H)-one in the form of a viscous oil.

N, calculated: 33.2%
N, found: 33.1%

The following may be mentioned individually as new active compounds: 4-amino-6-sec.-butyl-3-methylthio-1,2,4-triazin-5(4H)-one, 4-amino-6-sec.-butyl-3-methylamino-1,2,4-triazin-5(4H)-one, 4-amino-6-sec.-butyl-3-dimethylamino-1,2,4-triazin-5(4H)-one, 4-ethylideneamino-6-sec.-butyl-3-methylthio-1,2,4-triazin-5(4H)-one, 4-propylideneamino-6-sec.-butyl-3-methylthio-1,2,4-triazin-5(4H)-one, 4-isopropylideneamino-6-sec.-butyl-3-methylthio-1,2,4-triazin-5(4H)-one, 4-butyl-ideneamino-6-sec.-butyl-3-methylthio-1,2,4-triazin-5(4H)-one, 4-sec.-butylideneamino-6-sec.-butyl-3-methylthio-1,2,4-triazin-5(4H)-one, 4-isobutylideneamino-6-sec.-butyl-3-methylthio-1,2,4-triazin-5 (4H)-one, 4-cyclopentylideneamino-6-sec.-butyl-3-methylthio-1,2,4-triazin-5(4H)-one, 4-cyclohexylideneamino-6-sec.-butyl-3-methylthio-1,2,4-triazin-5(4H)-one, 4-(3-phenylpropylideneamino)-6-sec.-butyl-3-methylthio-1,2,4-triazin-5(4H)-one, 4-(1-phenylethylideneamino)-6-sec.-butyl-3-methylthio-1,2,4-triazin-5(4H)-one, 4-[1-(3-nitrophenyl)-ethylideneamino]-6-sec.-butyl-3-methylthio-1,2,4-triazin-5(4H)-one, 4-[1-(4-chlorophenyl)-ethylideneamino]-6-sec.-butyl-3-methylthio-1,2,4-triazin-5(4H)-one, 4-hexahydrobenzylideneamino-6-sec.-butyl-3-methylthio-1,2,4-triazin-5(4H)-one, 4-cinnamylideneamino-6-sec.-butyl-3-methylthio-1,2,4-triazin-5(4H)-one, 4-benzylideneamino-6-sec.-butyl-3-methylthio-1,2,4-triazin-5(4H)-one, 4-(4-chlorobenzylideneamino)-6-sec.-butyl-3-methylthio-1,2,4-triazin-5(4H)-one, 4-(3-chlorobenzylideneamino)-6-sec.-butyl-3-methylthio-1,2,4-triazin-5(4H)-one, 4-(2,4-dichlorobenzylideneamino)-6-sec.-butyl-3-methylthio-1,2,4-triazin-5(4H)-one, 4-(3-nitrobenzylideneamino)-6-sec.-butyl-3-methylthio-1,2,4-triazin-5(4H)-one, 4-(4-nitrobenzylideneamino)-6-sec.-butyl-3-methylthio-1,2,4-triazin-5(4H)-one, 4-furfurylideneamino-6-sec.-butyl-3-methylthio-1,2,4-triazin-5(4H)-one, 4-isopropylideneamino-3-methylamino-6-sec.-butyl-1,2,4-triazin-5(4H)-one, 4-isobutylideneamino-3-methylamino-6-sec.-butyl-1,2,4triazin-5(4H)-one, 4-cyclohexylideneamino-3-methylamino-6-sec.-butyl-1,2,4-triazin-5(4H)-one, 4-benzylideneamino-3-methylamino-6-sec.-butyl-1,2,4-triazin-5(4H)-one, 4-(4-chlorobenzylideneamino)-3-methylamino-6-sec.-butyl-1,2,4-triazin-5(4H)-one, 4-furfurylideneamino-3-methylamino-6-sec.-butyl-1,2,4-triazin-5(4H)-one, 4-isopropylideneamino-3-dimethylamino-6-sec.-butyl-1,2,4-triazin-5(4H)-one, 4-isobutylideneamino-3-dimethylamino-6-sec.-butyl-1,2,4-triazin-5 (4H)-one, 4-benzylideneamino-3-dimethylamino-6-sec.-butyl-1,2,4-triazin-5(4H)-one, 4-cyclohexylideneamino-3-dimethylamino-6-sec.-butyl-1,2,4-triazin-5(4H)-one and 4-furfurylideneamino-3-dimethylamino-6-sec.-butyl-1,2,4-triazin-5(4H)-one.

The active compounds according to the invention, of the formula (I), have a very good herbicidal activity and can therefore be used for combating weeds.

Weeds in the broadest sense are to be understood as all plants which grow in locations where they are not desired. Weeds concerned are, in particular: dicotyledons, such as mustard (Sinapis), cress (Lepidium), cleavers (Galium), chickweed (Stellaria), camomile (Matricaria), gallant soldier (Galinsoga), goosefoot (Chenopodium), annual nettle (Urtica), knotweed (Polygonum), groundsel (Senecio) and rough-haired amaranth (*Amaranthus retroflexus*), and monocotyledons such as timothy (Phleum), bluegrass (Poa), fescue (Festuca), goosegrass (Eleusine), foxtail (Setaria), ryegrass (Lolium), cheat (Bromus), barnyard grass (Echinochloa), wild oats (*Avena fatua*), foxtail grass (Alopecurus) and Johnson grass (*Sorghum halepense*).

As already emphasized above, the active compounds according to the invention are particularly effective in combating cleavers (*Galium aparine*), which is very resistant. The active compounds according to the invention are also preferentially suitable for the selective combating of weeds, for example in soya beans, potatoes, tomatoes, maize and cereals, because they are well tolerated by these crops.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g., aerosol propellants, such as halogenated hydrocarbons, e.g., freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin, sulfite waste liquors and methyl cellulose.

The active compounds according to the invention can be used as a mixture with other active compounds.

The formulations in general contain 0.1 to 95 percent by weight of active compound, preferably 0.5 to 90 percent.

The active compounds can be used as such or in the form of their formulations or as the use forms prepared therefrom, such as ready-to-use solutions, emulsions, suspensions, powders, pastes and granules. They may be applied in the customary manner, for example by spraying, atomizing, dusting, scattering and watering.

The active compounds according to the invention can be used both in the pre-emergence and in the post-emergence methods.

The compositions may be diluted for actual application. The amount of active compound employed can be varied within substantial ranges. It depends essentially on the nature of the desired effect. In general, the active compound is applied to an area of agriculture in an amount of 0.05 to 10 kg/hectare, preferably 0.1 to 5 kg/hectare.

The invention therefore provides a herbicidal composition containing as active ingredient a compound according to the invention in admixture with a solid or liquefied gaseous diluent or carrier containing a surface-active agent.

with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denote:

0% = no effect

100% = total destruction

The active compounds, the amounts applied and the results can be seen from Table A:

Table A

| Active compound | Pre-emergence test/in the open | | | | | | | |
|---|---|---|---|---|---|---|---|---|
| | Amount used kg/ha | Potatoes | Soya | Maize | Stellaria | Cheno- podium | Fumaria | Galium aparine |
| 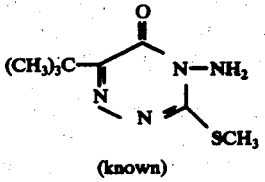 (known) | 0.5 0.70 | 0 0 | 0 0 | 0 10 | 100 100 | 100 100 | 100 100 | 20 25 |
| 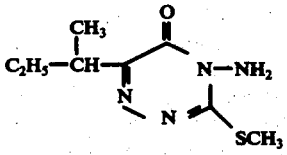 | 0.5 0.70 | 0 0 | 0 0 | 0 0 | 100 100 | 100 100 | 100 100 | 97 100 |

The invention also provides a method of combating weeds which comprises applying to the weeds or their habitat a compound according to the invention alone or in the form of a composition containing as active ingredient a compound according to the invention in admixture with a diluent or carrier.

The invention also provides means of yielding crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples:

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5 - 15 cm were sprayed with the preparation of the active compound in such a way as to apply the amounts of active compound per unit area which are indicated in the table.

Depending on the concentration of the spray liquor, the amount of water used was between 1,000 and 2,000 l/ha. After three weeks, the degree of damage to the plants was rated in % damage in comparison to the development of the untreated control. The figures denote:

0% = no effect

100% = total destruction

The active compounds, the amounts applied and the results can be seen from Table B:

Table B

| | | Post-emergence/greenhouse | | | | |
|---|---|---|---|---|---|---|
| Active compound | Amount used, kg/ha | Potatoes | Barley | Chenopodium | Poa annua | Galium aparine |
| n-C$_4$H$_9$ structure (not claimed) | 0.5 | 0 | 30 | 100 | 100 | 50 |
| | 0.25 | 0 | 10 | 100 | 100 | 30 |
| iso-C$_4$H$_9$ structure (known) | 0.5 | 0 | 30 | 100 | 100 | 50 |
| | 0.25 | 0 | 10 | 100 | 100 | 30 |
| tert.C$_4$H$_9$ structure (known) | 0.5 | 0 | 30 | 100 | 100 | 50 |
| | 0.25 | 0 | 10 | 100 | 100 | 20 |
| sec-C$_4$H$_9$ structure (according to the invention) | 0.5 | 0 | 10 | 100 | 100 | 100 |
| | 0.25 | 0 | 10 | 100 | 100 | 95 |

It will be appreciated that the instant specification and examples are set forth by way of illustration and not limitation, and that various modifications and changes may be made without departing from the spirit and scope of the present invention.

What is claimed is:

1. A compound selected from the group consisting of 4-amino-6-sec.-butyl-3-methylthio-1,2,4-triazin-5(4H)-one,
4-benzylideneamino-6-sec.-butyl-3-methylthio-1,2,4-triazin-5(4H)-one,
4-isobutylideneamino-6-sec.-butyl-3-methylthio-1,2,4-triazin-5(4H)-one, and
4-furfurylidene-amino-6-sec.-butyl-3-methylthio-1,2,4-triazin-5(4H)-one.

2. A compound according to claim 1, wherein such compound is 4-amino-6-sec.-butyl-3-methylthio-1,2,4-triazin-5(4H)-one.

3. A compound according to claim 1, wherein such compound is 4-benzylideneamino-6-sec.-butyl-3-methylthio-1,2,4-triazin-5(4H)-one.

4. A compound according to claim 1, wherein such compound is 4-isobutylideneamino-6-sec.-butyl-3-methylthio-1,2,4-triazin-5(4H)-one.

5. A compound according to claim 1, wherein such compound is 4-furfurylidene-amino-6-sec.-butyl-3-methylthio-1,2,4-triazin-5(4H)-one.

6. A method of controlling Galium aparine which comprises applying to the locus thereof an effective amount of a compound according to claim 2.

7. A method of controlling Galium aparine which comprises applying to the locus thereof an effective amount of a compound according to claim 3.

8. A method of controlling Galium aparine which comprises applying to the locus thereof an effective amount of a compound according to claim 4.

9. A method of controlling Galium aparine which comprises applying to the locus thereof an effective amount of a compound according to claim 5.

10. A herbicidal composition comprising a herbicidially effective amount of a compound according to claim 2 in admixture with an inert diluent.

11. A herbicidal composition comprising a herbicidally effective amount of a compound according to claim 3 in admixture with an inert diluent.

12. A herbicidal composition comprising a herbicidally effective amount of a compound according to claim 4 in admixture with an inert diluent.

13. A herbicidal composition comprising a herbicidally effective amount of a compound according to claim 5 in admixture with an inert diluent.

* * * * *